United States Patent [19]

Poovaiah et al.

[11] Patent Number: 5,498,533

[45] Date of Patent: Mar. 12, 1996

[54] CONTROL OF GROWTH AND DEVELOPMENT OF POTATO PLANTS

[75] Inventors: Bachettira W. Poovaiah, Pullman, Wash.; Daisuke Takezawa, Osaka, Japan; Tae-Jin Han, Kyung Ki Do, Rep. of Korea; Gynheung H. An, Pullman, Wash.

[73] Assignee: Washington State University Research Foundation, Pullman, Wash.

[21] Appl. No.: 100,874

[22] Filed: Jul. 30, 1993

[51] Int. Cl.$^6$ .............................. C12N 15/00; A01H 1/04
[52] U.S. Cl. .................... 435/172.3; 435/69.1; 435/70.1; 800/205; 800/DIG. 42
[58] Field of Search ........................... 800/205, DIG. 42; 435/172.3, 69.1, 240.4, 240.51, 70.1; 47/58

[56] References Cited

FOREIGN PATENT DOCUMENTS 0281374  2/1988  European Pat. Off. ......... A01G 7/00

OTHER PUBLICATIONS

Arteca, R. N. et al., "Changes in Carbon Fixation, Tuberization, and Growth Induced by $CO_2$ Applications to the Root Zone of Potato Plants," *Science*, 205:1279–1280 (1979).
Balamani, V. et al., "Effect of Calcium on Tuberization in Potato (*Solanum tuberosum* L.)[1]", *Plant Physiol.*, 80:856–858 (1986).
Dietrich, B., The Seattle Times, "Bold New Splashes in the Gene Pool," Apr. 13, 1993.
Hepler, P. K. et al., "Calcium and Plant Development," *Ann. Rev. Plant Physiol.*, 36:397–439 (1985).
Jean, P. K. et al., "Molecular cloning and sequencing of a cDNA for plant calmodulin: Signal–induced changes in the expression of calmodulin," *PNAS (USA)*, 86:3644–3648 (1989).
Poovaiah, B. W. et al., "Calcium Messenger System In Plants," *Crit. Rev. Plant Scien.*, 6(1):47–102 (1987).
Poovaiah, B. W. et al., "Calcium messenger system: Role of protein phosphorylation and inositol phospholipids," *Physiol. Plant*, 69:569–573 (1987).
Poovaiah, B. W. et al., "Calcium and Signal Transduction in Plants," *Crit. Rev. Plant Scien.*, 12(3):185—211 (1993).
Poovaiah, B. W. et al., "Potato Plants Carrying Sense and Antisense Constructs of Calmodulin Exhibit Striking Differences in Growth and Development," *Plant Physiol. Suppl.*, vol. 102, No. 1, Abstract 67 (1993).
Ranjeva, R. et al., "Phosphorylation of Proteins in Plants: Regulatory Effects and Potential Involvement in Stimulus/Response Coupling," *Ann. Rev. Plant Physiol.*, 38:73–93 (1987).
Roberts, D. M. et al., "Structure, Function, and Mechanism of Action of Calmodulin," *Crit. Rev. Plant Scien.*, 4(4):311–339 (1986).
Roux, S. J. et al., "Cellular Mechanisms Controlling Light–Stimulated Gravitropism: Role of Calcium," *CRC Crit. Rev. Plant Scien.*, 5(3):205–236 (1987).
Veluthambi, K. et al., "Calcium–Promoted Protein Phosphorylation in Plants," *Science*, 223:167–169 (1984).
Wang, Z. et al., "Transformation of Tobacco with Sense and Antisense Constructs of Calmodulin," *Plant Physiol. Suppl.*, 93:157 Abstract 914 (1990).
Köster–Topfer et al. (1989) Mol Gen Genet. 219:390–396.
Roberts et al. (Sep. 1992) Proc Natl Acad Sci USA 89:8394–8398.
Larkins et al. (1985) J Cell Biochem Suppl. O (9 part C) p. 264.

*Primary Examiner*—David T. Fox
*Assistant Examiner*—Elizabeth F. McElwain
*Attorney, Agent, or Firm*—Harness, Dickey & Pierce

[57] ABSTRACT

A method of controlling growth and development of plants is provided herein. More particularly, a method of controlling growth and development of potato plants by increasing or decreasing the expression of a gene encoding calmodulin is set forth. Transgenic potato plants carrying sense nucleic acid constructs of pPCM-1, a cDNA clone of potato calmodulin, exhibit unexpected increased shoot and tuber growth, whereas plants carrying antisense nucleic acid constructs exhibit decreased shoot and tuber growth.

6 Claims, 8 Drawing Sheets

FIGURE 1

```
  1 TTTTGAGGAG AGAGATAAAA CTCAAATCAC ATACATATTA GTACTTAACT
 51 GTACAGCTGT TTCTAGGAGT ACGAAAAAAA ATGGCAGAGC AGCTGACGGA
101 GGAGCAGATC GCCGAGTTCA AGGAAGCTTT TAGCCTTTTC GACAAGGATG
151 GCGATGGCTG TATTACTACC AAGGAGTTGG AACAGTGAT GAGATCACTT
201 GGTCAGAATC CCACTGAAGC TGAACTACAG GATATGATCA GTGAAGCTGA
251 TGCTGATCAG AATGGAACCA TTGATTTTCC AGAGTTCTTG AATCTGATGG
301 CACGTAAGAT GAAGGACACT GATTCTGAGG AGGAACTCAA AGAGGCTTTC
351 AAGGTTTTCG ATAAAGATCA GAATGGCTTT ATTTCTGCAG CTGAGCTTCG
401 TCATGTAATG ACAAACCTTG AGAGAAGCT GACTGATGAA GAGGTGGATG
451 AGATGATCCG AGAGGCAGAT ATTGATGGTG ATGGGCAAGT TAATTATGAG
501 GAGTTTGTCC GTATGATGCT TGCCAAGTGA TGGCTTAAGA TTCTCTTAGC
551 TACTGTCTAA TTTATGATGG CCGCTTAGTT ACTACAACTT CTAGCTGGCA
601 GTTATATTCT GTTCTGTTAA GACAAACAAA TGTGTCGTAT GGTTTTACTA
651 GCATCTAGAC TCCTTTCAGT TTTATGTTAA CTTATGGACT ACAGGTGTAT
701 GCTGCTTTAG TCCCTTGCCC ATCCAGAGGG GAAAAGAAAA GGAGAAATTA
751 GATAGTTCAT TCGTAATATC TTGTTAGTTG CCTTGGTTTC TTTCCAGGCT
801 ACAGTCTGTA TGTGTTTCAC TGTCTCTAAC TGTTATATTT CCCGTTTCTG
851 GTTTTCGCTT TTATCACTGA TTAATGGGAA GGTCAAATGC AAGGTGATTA
901 TTTCCT
```

FIGURE 2

```
1         .         .         .         .         .         60
TTTTGAGGAGAGAGATAAAACTCAAATCACATACATATTAGTACTTAACTGTACAGCTGT

61        .         .         .         .         .        120
TTCTAGGAGTACGAAAAAAAATGGCAGAGCAGCTGACGGAGGAGCAGATCGCCGAGTTCA
                   M  A  E  Q  L  T  E  E  Q  I  A  E  F  K

121       .         .         .         .         .        180
AGGAAGCTTTTAGCCTTTTCGACAAGGATGGCGATGGCTGTATTACTACCAAGGAGTTGG
 E  A  F  S  L  F  D  K  D  G  D  G  C  I  T  T  K  E  L  G

181       .         .         .         .         .        240
GAACAGTGATGAGATCACTTGGTCAGAATCCCACTGAAGCTGAACTACAGGATATGATCA
 T  V  M  R  S  L  G  Q  N  P  T  E  A  E  L  Q  D  M  I  S

241       .         .         .         .         .        300
GTGAAGCTGATGCTGATCAGAATGGAACCATTGATTTTCCAGAGTTCTTGAATCTGATGG
 E  A  D  A  D  Q  N  G  T  I  D  F  P  E  F  L  N  L  M  A

301       .         .         .         .         .        360
CACGTAAGATGAAGGACACTGATTCTGAGGAGGAACTCAAAGAGGCTTTCAAGGTTTTCG
 R  K  M  K  D  T  D  S  E  E  E  L  K  E  A  F  K  V  F  D

361       .         .         .         .         .        420
ATAAAGATCAGAATGGCTTTATTTCTGCAGCTGAGCTTCGTCATGTAATGACAAACCTTG
 K  D  Q  N  G  F  I  S  A  A  E  L  R  H  V  M  T  N  L  G

421       .         .         .         .         .        480
GAGAGAAGCTGACTGATGAAGAGGTGGATGAGATGATCCGAGAGGCAGATATTGATGGTG
 E  K  L  T  D  E  E  V  D  E  M  I  R  E  A  D  I  D  G  D

481       .         .         .         .         .        540
ATGGGCAAGTTAATTATGAGGAGTTTGTCCGTATGATGCTTGCCAAGTGATGGCTTAAGA
 G  Q  V  N  Y  E  E  F  V  R  M  M  L  A  K

541       .         .         .         .         .        600
TTCTCTTAGCTACTGTCTAATTTATGATGGCCGCTTAGTTACTACAACTTCTAGCTGGCA

601       .         .         .         .         .        660
GTTATATTCTGTTCTGTTAAGACAAACAAATGTGTCGTATGGTTTTACTAGCATCTAGAC

661       .         .         .         .         .        720
TCCTTTCAGTTTTATGTTAACTTATGGACTACAGGTGTATGCTGCTTTAGTCCCTTGCCC

721       .         .         .         .         .        780
ATCCAGAGGGGAAAAGAAAAGGAGAAATTAGATAGTTCATTCGTAATATCTTGTTAGTTG

781       .         .         .         .         .        840
CCTTGGTTTCTTTCCAGGCTACAGTCTGTATGTGTTTCACTGTCTCTAACTGTTATATTT

841       .         .         .         .         .        900
CCCGTTTCTGGTTTTCGCTTTTATCACTGATTAATGGGAAGGTCAAATGCAAGGTGATTA

906
TTTCCT
```

CONTROL OF GROWTH AND DEVELOPMENT OF POTATO PLANTS

FIELD OF THE INVENTION

The present invention relates to a method of controlling growth and development of plants. More particularly, this invention relates to a method of controlling growth and development of potato plants by increasing or decreasing the expression of a gene encoding calmodulin.

BACKGROUND OF THE INVENTION

Signals such as hormones, light, and gravity control diverse physiological processes in plants. Thimann, K. V., *Hormone Action in the Whole Life of Plants* (Univ. Mass. Press, Amherst) (1977); Leopold, A. C et al., *Plant Growth and Development* (McGraw-Hill, New York) (1975). Although the biochemical and molecular events involved in the transduction of these signals are not clearly understood, calcium is known to act as a messenger in signal transduction. Helper, P. K. et al., *Annu. Rev. Plant Physiol.* 36:397–439 (1985); Poovaiah, B. W. et al., *CRC Crit. Rev. Plant Sci.* 6, 47– 103 (1987); Poovaiah, B. W. et al., *Physiol. Plant.* 69:569–573 (1987); Roux, S. J. et al., *CRC Crit. Rev. Plant Sci.* 5:205–236 (1987). As in animals, many of the effects of calcium ions in plant cells are mediated by a calcium-binding regulatory protein, calmodulin. Roberts, D. M. et al., *CRC Crit. Rev. Plant Sci.* 4:311–339 (1986). Calmodulin is a highly conserved, heat-stable, acidic protein with four calcium-binding domains. Poovaiah, B. W. et al., *CRC Crit. Rev. Plant Sci.* 6:47–103 (1987); Roberts, D. M. et al., *CRC Crit. Rev. Plant Sci.* 4:311–339 (1986). Calmodulin binds to calcium, undergoing a conformational change, and then interacts with enzyme-molecules. The $Ca^{2+}$-calmodulin complex can regulate enzyme activities directly and indirectly through protein phosphorylation by activating protein kinases. Poovaiah, B. W. et al., *CRC Crit. Rev. Plant Sci.* 6:47–103 (1987); Roberts, D. M. et al., *CRC Crit. Rev. Plant Sci.* 4:311–339 (1986); Veluthambi, K. et al., *Science* 223:167–169 (1984); Ranjeva, R. et al.; *Annu. Rev. Plant Physiol.* 38:73–93 (1987). In plants, enzymes such as NAD kinase, $Ca^{2+}$-ATPase, $H^+$-ATPase, quinate:$NAD^+$ oxidoreductase and protein kinases have been shown to be regulated by calcium and calmodulin. Poovaiah, B. W. et al., *CRC Crit. Rev. Plant Sci.* 6:47–103 (1987); Roberts, D. M. et al., *CRC Crit. Rev. Plant Sci.* 4:311–339 (1986).

The structure of the calmodulin gene and its expression have been well studied in animals. Means, A. R. et al., *Calcium and Cell Physiology*, ed. Marme, D. (Springer, New York) 127–139 (1985); Mujaal, R. P et al., *Proc. Natl. Acad. Sci. USA* 78:2330–2334 (1981 ); Lagace, L. et al., *J. Biol. Chem.* 258:1684–1688 (1983); Putkey, J. A. et al., *J. Biol. Chem.* 258:11864–11 870 (1983). In animal cells, intracellular levels of calmodulin have been shown to be unaffected by a number of steroid and peptide hormones. Means, A. R. et al., *Physiol. Rev.* 62:1–38 (1982). However, calmodulin levels were found to be elevated in transformed cells and also at the $G_1$/S boundary of the growth cycle of mammalian cells. Chafouleas, J. G. et al., *Cell* 28:41–50 (1982); Chafouleas, J. G. et al., *Cell* 36:73–81 (1984); Chafouleas, J. G. et al., *Proc. Natl. Acad. Sci. USA* 78:996–1000 (1981 ); Zendegui, J. G. et al., *Mol. Cell. Biol.* 4:883–889 (1984). In these cases, the changes in calmodulin were found to be accompanied or preceded by changes in the level of its mRNA. Chafouleas, J. G. et al., *Cell* 36:73–81 (1984); Zendegui, J. G. et al., *Mol. Cell. Biol.* 4:883–889 (1984).

Calmodulin protein has also been studied in plants. In particular, a calmodulin protein in plants has been isolated and characterized. Poovaiah, B. W. et al., *CRC Crit. Rev. Plant Sci.* 6:47–103 (1987); Roberts, D. M. et al., *CRC Crit. Rev. Plant Sci.* 4:311– 339 (1986). To further understand calmodulin gene expression in plants, a plant calmodulin cDNA clone (pPCM-1) has been isolated and sequenced. Jena, P. K. et al., *PNAS* (USA) 86:3644–3648 (1989). By using the cDNA clone, it has been shown that signals such as auxin and light regulate the expression of calmodulin. Jena, P. K. et al., *PNAS* (USA) 86:3644–3648 (1989). To further study the role of plant calmodulin, particularly the consequences of altered levels of intracellular calmodulin, several independent transgenic tobacco plants expressing either sense or antisense calmodulin mRNA driven by the cauliflower mosaic virus (CaMV) 35S promoter have been generated. Wang, A. et al., *Plant Physiol. Suppl.* 93:914 (1990). There were no abnormalities in growth or development in these sense and antisense transgenic plants.

In potato plants, the role of calcium and calmodulin in the tuberization process has been studied. Balamani, V. et al., Plant Physiol. 80:856–858 (1986); Balamani, V. et al., *Plant Physiol.* 80:856–858 (1986); Jena, P. K. et al., *PNAS* (USA) 86:3644–3648 (1989). In particular, it has been shown that increased intracellular calcium levels increases tuberization. Balamani, V. et al., *Plant Physiol.* 80:856–858 (1986). Potatoes are a major food crop in the United States and therefore, controlling tuberization by genetically altering potato plants would be very desirable.

It would thus be desirable to control growth and development of plants. It would also be desirable to control growth and development of plants by controlling the expression of a gene encoding calmodulin. It would also be desirable to control growth and development of potato plants by controlling the expression of a gene encoding calmodulin. It would further be desirable to control growth and development of plants without employing chemicals foreign to the plant. It would also be desirable to acquire long-term control of growth and development of plants by genetically altering the plants,

SUMMARY OF THE INVENTION

Figure 1:
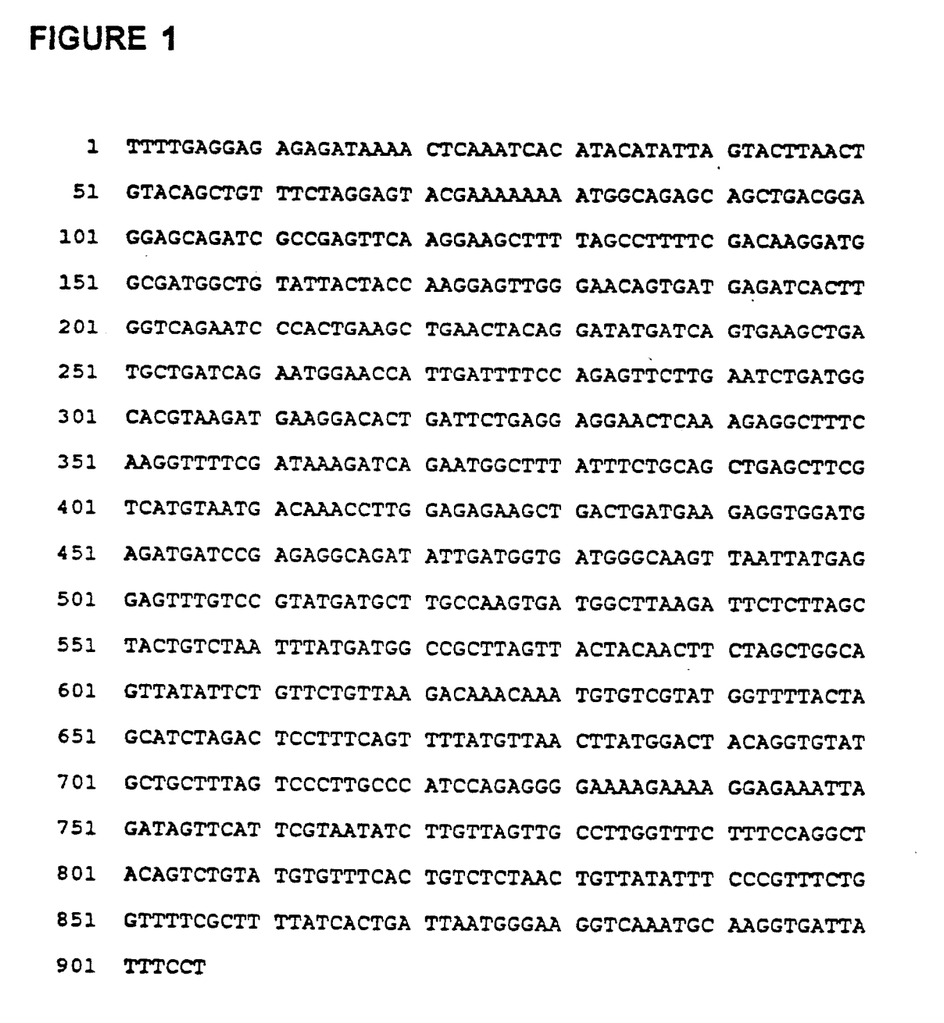
FIG. 1 is the nucleic acid sequence of pPCM-1.
Figure 2:
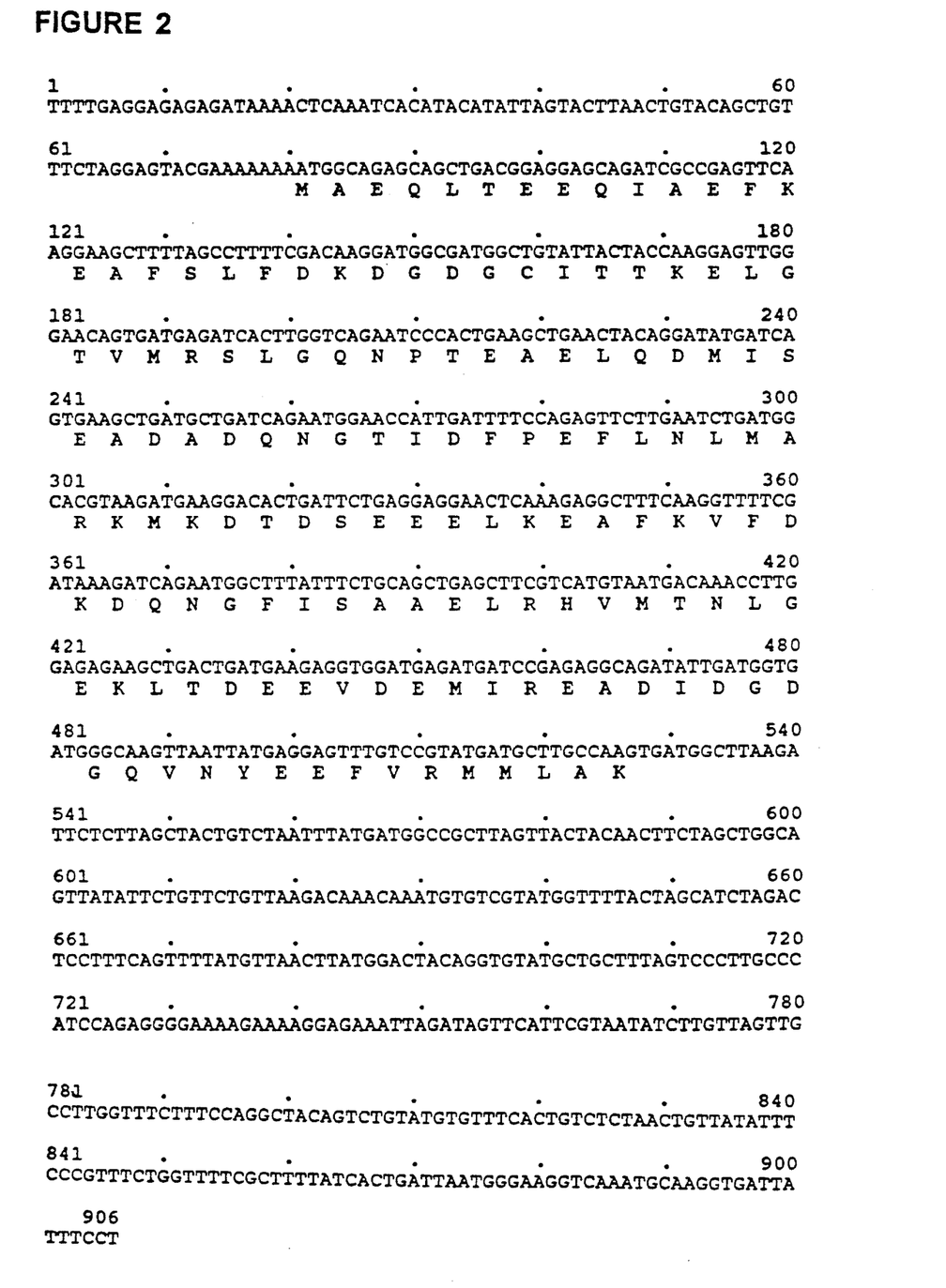
FIG. 2 is the nucleic acid and corresponding amino acid sequence of pPCM-1.

A method of controlling growth and development of plants, in particular potato plants, by inducing or suppressing the expression of a gene encoding calmodulin is disclosed herein. Transgenic potato plants carrying sense strand nucleic acid or antisense strand nucleic acid constructs of a cDNA clone, pPCM-1, for potato calmodulin, have been produced. The nucleic acid and amino acid sequences for pPCM-1 are set forth in Sequence Listing IDs 1 and 2, respectively, and have been accorded Genbank accession number J04559. The nucleic acid and amino acid sequences are also set forth in FIGS. 1 and 2, respectively.

An unexpected and dramatic difference has been observed in the growth and development of the potato plants carrying the sense strand or antisense strand constructs. For example, plants carrying an antisense construct exhibit a reduction in both shoot growth and tuber growth whereas plants carrying a sense construct exhibit stimulation of both shoot growth and tuber growth. Second generation plants produced from tubers of transgenic plants also show similar growth patterns.

A set of transgenic potato plants carrying sense or antisense strand constructs of calmodulin fused to an inducible promoter (patatin) have also been produced in accordance with the principles of the present invention. In these transgenic plants, there was also a dramatic difference in the tuberization pattern. For example, plants carrying antisense construct formed tubers readily, in contrast to the dramatic delay of tuberization in other plants.

The method of the present invention includes introducing the sense or antisense strand constructs of pPCM-1 into a plant cell, and growing the cell into a callus and then into a plant; or, alternatively, breeding a transgenic plant produced from the above method with a second plant to form an F1 or higher hybrid (e.g. F2). The transgenic plants of the present invention can be produced by this method.

The method of the present invention is thus useful for the regulation of plant growth and development. The present invention provides a method of enhancing growth and development of plants, in particular potato plants, by introducing a calmodulin sense nucleic acid construct of pPCM-1 into a plant cell. The present invention also provides a method for inhibiting growth and development by introducing an antisense strand nucleic acid construct of pPCM-1 into a plant cell. Transgenic potato plants containing the calmodulin constructs are also provided. Those skilled in the art will recognize the agricultural advantages inherent in the transgenic plants of the present invention, for example, increased tuber size in potatoes.

Although the method of the present invention is described in conjunction with potato plants, those skilled in the art will readily appreciate that the teachings of the present invention may also be used to control growth and development in plants other than potato plants.

Additional objects, advantages, and features of the present invention will become apparent from the following description and appended claims, taken in conjunction with the accompanying drawings.

BRIEF DESCRIPTION OF THE DRAWINGS

The various advantages of the present invention will become apparent to one skilled in the art by reading the following specification and subjoined claims and by referencing the following drawings in which:

DETAILED DESCRIPTION OF THE PREFERRED EMBODIMENTS

A method of controlling growth and development of plants, in particular potato plants, by increasing or decreasing the expression of a gene encoding calmodulin is provided. Transgenic plants carrying sense or antisense strand constructs of potato calmodulin have been produced. Growth and development of potato plants has been controlled by administering sense nucleic acid or antisense nucleic acid constructs of the cDNA clone pPCM-1 for plant calmodulin. Although an increase in stem and tuber elongation in transgenic plants carrying the sense construct was observed, only a moderate increase in calmodulin mRNA was detected. A retardation of stem and tuber elongation in transgenic plants carrying antisense constructs of calmodulin was also observed.

A set of transgenic plants carrying sense or antisense nucleic acid constructs fused to an inducible promoter, patatin have also been produced. In these plants, the antisense plants formed tubers readily whereas tuberization was delayed in sense plants.

As referred to herein, the term "gene" is meant a nucleic acid, either genomic or synthetic, which encodes a protein product. The term "nucleic acid" is intended to mean natural and synthetic linear and sequential arrays of nucleotides and nucleosides, e.g. in cDNA, genomic DNA (gDNA), mRNA, and RNA, oligonucleotides, oligonucleosides, and derivatives thereof. For ease of discussion, such nucleic acids are at times collectively referred to herein as "constructs," "plasmids" or "vectors." The term "sense strand" as used herein refers to a single-stranded DNA molecule from DNA that is transcribable and translatable into the polypeptide product of the gene. The term "antisense strand" is used to mean the single strand DNA molecule of DNA that is complementary to the sense strand of the gene. In addition, the term "encoding" is intended to mean that the subject nucleic acid may be transcribed and translated into either the desired polypeptide or the subject protein in an appropriate expression system, e.g. when the subject nucleic acid is linked to appropriate control sequences such as promoter and enhancer elements in a suitable vector (e.g. an expression vector) and when the vector is introduced into an appropriate system or cell. By "substantially as shown" or "substantially similar" with respect to a nucleic acid is meant sufficiently similar in structure or sequence to encode the desired polypeptide or protein product.

The following Specific Examples describe in further detail the present invention.

SPECIFIC EXAMPLE 1—cDNA CLONE

The cDNA clone pPCM-1 for plant calmodulin was isolated by screening a potato stolon tip cDNA library with a chicken calmodulin cDNA. The nucleic acid and amino acid sequences of the potato calmodulin are set forth in Sequence Listing IDs 1 and 2, respectively and in FIGS. 1 and 2, respectively. Nucleotide sequence analysis of pPCM-1 revealed that it contained 80 base pairs of 5' untranslated region, the entire coding region, and 376 base pairs of 3' untranslated region. Comparison of the nucleotide sequence of coding regions of potato and chicken calmodulin mRNA showed 78% homology. Comparison of the predicted amino acid sequence of potato calmodulin with other known calmodulin sequences indicated a high degree of homology with a few exceptions. Three changes in the amino acid sequence were found to be unique to the potato calmodulin sequence. The sequence for pPCM-1 is also set forth in Jena, P. K. et al., *PNAS* (USA) 86:3644-3648 (1989), incorporated herein by reference.

SPECIFIC EXAMPLE 2—PLASMID CONSTRUCTION AND TRANSFORMATION

The expression vector used was the binary vector Ti-plasmid pGA748 which was derived from pGA643 by replacing the small HindlII-Cla1 fragment with a synthetic oligonucleotide containing multiple cloning sites. The EcoRI site at the left border of pGA643 was destroyed by filling in the sticky ends with dNTPs and DNA polymerase Klenow fragment before addition of the oligonucleotide. The resulting plasmid pGA748 carries seven unique restriction sites (HindlII-Sca1-Mlu-Xho1-EcoRI-Cla1-Bgl11) between the CaMV 35S promoter and the terminator of gene 7. As described above, the potato calmodulin cDNA clone, pPCM-1 which contains the entire coding region as well as the 5' and 3' untranslated regions was used. More specifically, the 636 bp Sca1-Hpa1 fragment containing the calmodulin ORF was used for construction of two plasmids by inserting into the Sca1 site of pGA748. Plasmid pGA924 contains the sense calmodulin ORF and plasmid pGA925 carries the antisense strand.

The binary plasmids pGA924 and pGA925 were transferred into *Agrobacterium tumefaciens* LBA4404 by direct DNA transfer method. Russet Burbank stem sections of sterile potato plants were co-cultivated with the Agrobacterium strain carrying the pGA plasmid and kanamycin-resistant shoots were selected in MS medium. Among the transgenic plants, seven transformants which showed variations in growth and development were studied in detail.

Figure 3A:
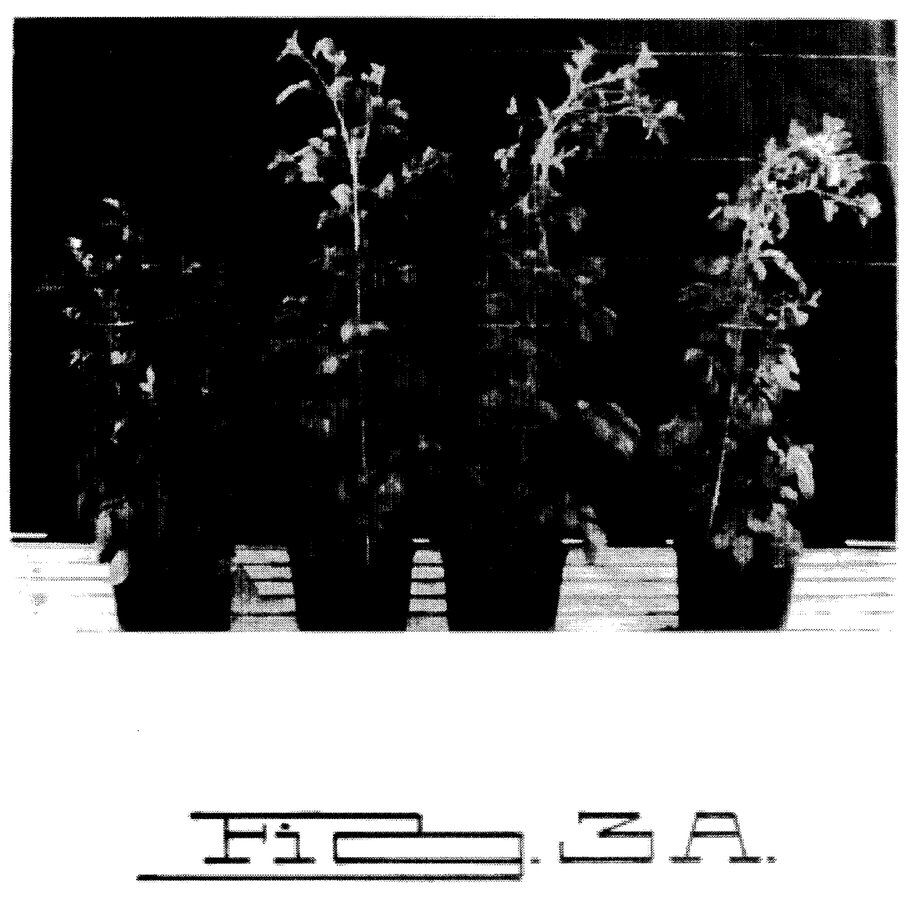
FIG. 3A is a photograph of a control and three independent transgenic plants carrying sense strand constructs of calmodulin.

To produce transgenic plants carrying the patatin promoter, the PBI101 plasmid was used. During plasmid construction, the GUS gene was replaced with the patatin promoter and the calmodulin sense or antisense nucleic acid construct. The constructs were again transferred into Agrobacterium tumefaciens LBA4404 by the direct DNA transfer method. Leaf strips of the potato line (FL1607) were used to generate transgenic plants. The results of the above described experiments are illustrated in FIGS. 3–7 and Table 1. FIG. 3A shows control and three independent transgenic plants carrying sense construct of calmodulin. In FIG. 3A, the plant on the left is the control and to the right are three transgenic plants. Table 1 sets forth the results of stem and internodal growth of plants carrying sense construct such as the plants shown in FIG. 3A. The measurements summarized in Table 1 were taken at harvest.

TABLE 1

Comparison Of Height And Internode Length Between Control And Transgenic Plants Carrying Sense Construct Of Calmodulin

| Plant | Average Height (cm) | Average Internode Length (cm) |
|---|---|---|
| Control Plants | 167.64 | 3.84 |
| Sense Plants | | |

TABLE 1-continued

Comparison Of Height And Internode Length Between Control And Transgenic Plants Carrying Sense Construct Of Calmodulin

| Plant | Average Height (cm) | Average Internode Length (cm) |
|---|---|---|
| S4 | 185.42 | 4.78 |
| S5 | 203.45 | 5.08 |
| S7 | 203.45 | 5.03 |

Figure 3B:
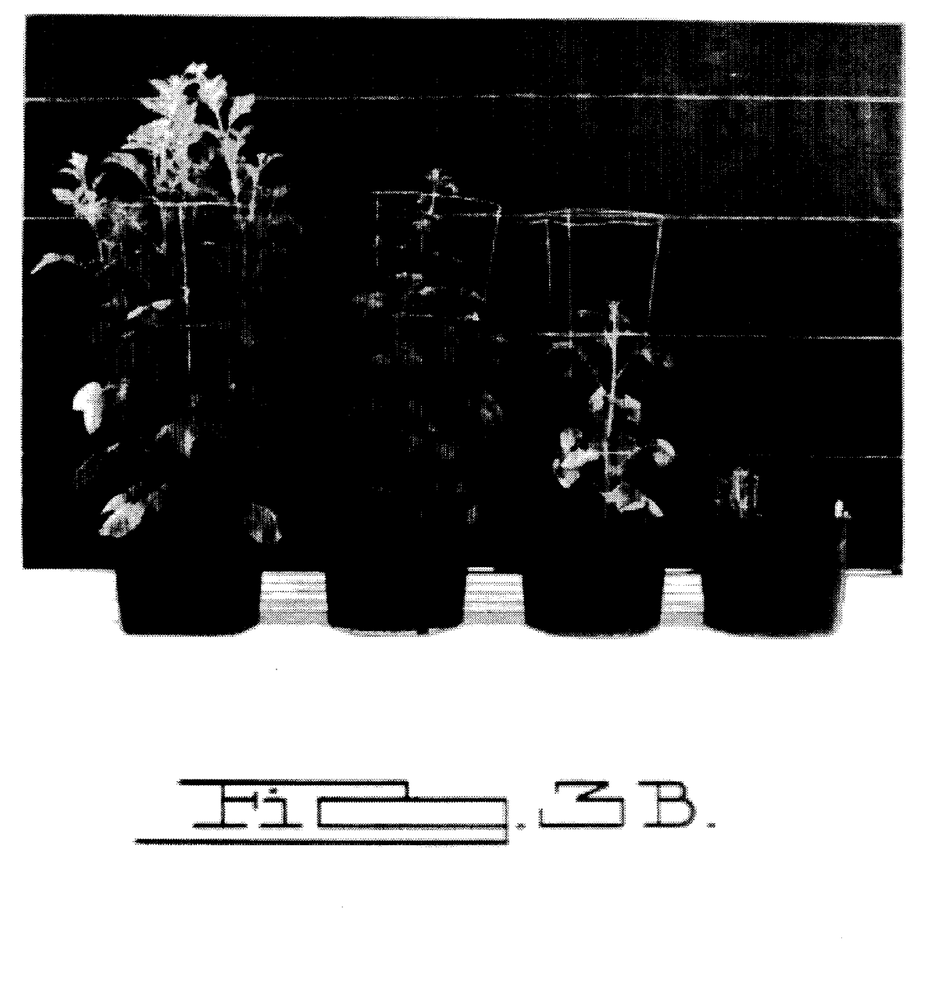
FIG. 3B is a photograph of a control and three independent transgenic plants carrying antisense strand constructs of calmodulin.

FIG. 3B shows control and three independent transgenic plants carrying antisense construct of calmodulin. In FIG. 3B, the plant on the left is the control and to the right are three transgenic plants. An increase in stem elongation in sense plants and drastic retardation of stem elongation in antisense plants can be seen in these figures.

Figure 4:
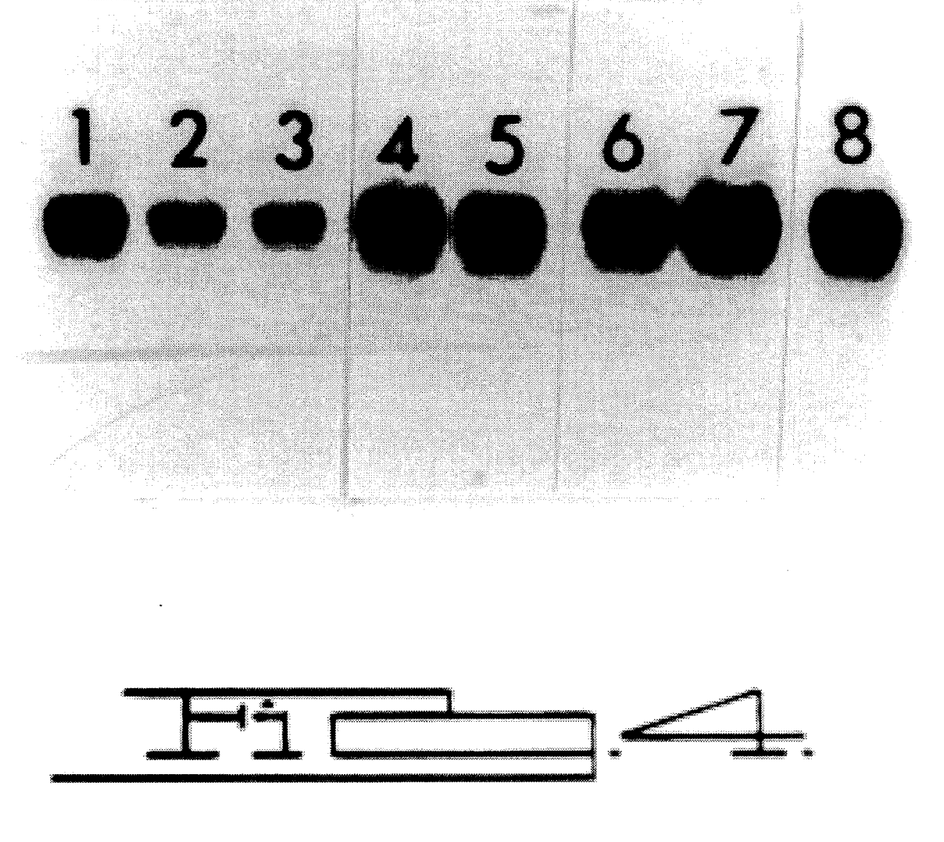
FIG. 4 is a Northern analysis showing calmodulin mRNA of the stem tissue of control plants, independent transgenic plants carrying antisense strand constructs of calmodulin and independent transgenic plants carrying sense strand constructs of calmodulin.

FIG. 4 is a Northern analysis showing calmodulin mRNA in the stem tissue of control (lane 1 ), two independent antisense plants, three independent sense plants, and two independent sense plants expressing the highest amounts of mRNA. In FIG. 4, lane 1 is the control; lanes 2 and 3 are the independent antisense plants from FIG. 3B, middle two plants; lanes 4–6 are the independent sense plants from FIG. 3A; and, lanes 7 and 8 are the independent sense plants expressing the highest amounts of mRNA. The mRNA samples were collected from plants from which the tubers were collected (see FIG. 5, described below) from the previous generation of sense plants shown in FIG. 3A. Unexpectedly, the set of sense plants expressing a moderate increase in calmodulin mRNA show increased stem elongation and also increased tuber elongation.

Figure 5:
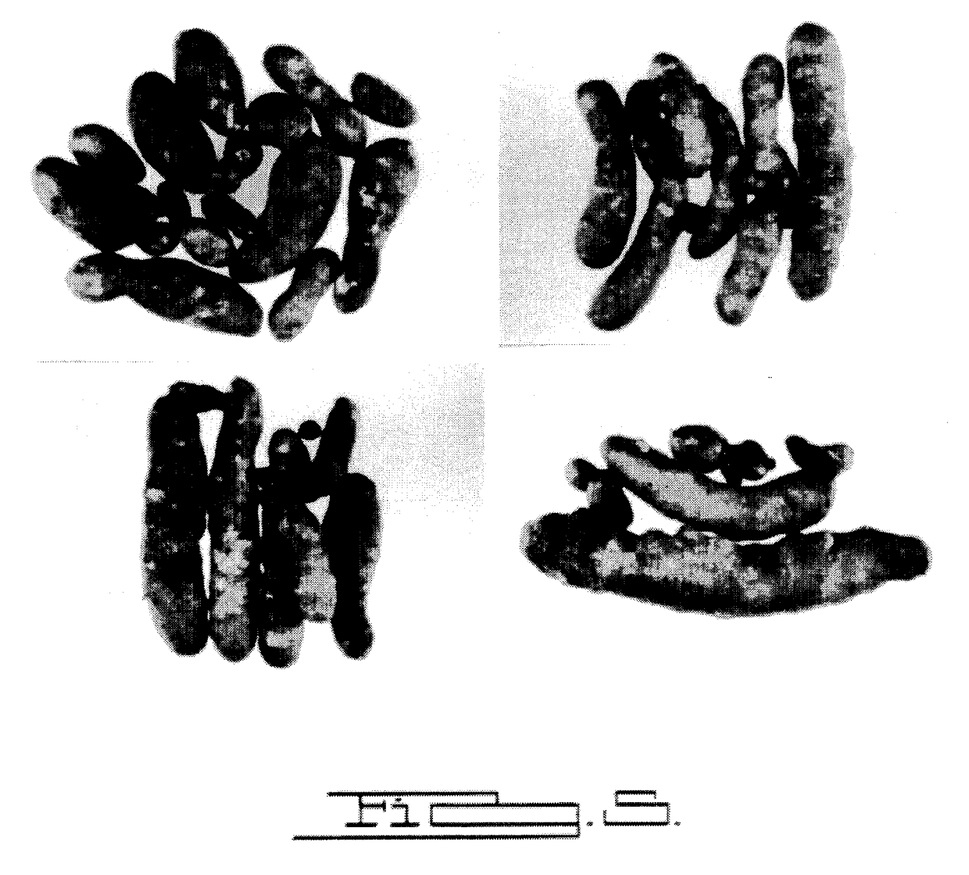
FIG. 5 is a photograph of potato tubers from control and independent transgenic plants carrying sense strand constructs of calmodulin.

FIG. 5 shows potato tubers from control (top left) and three independent transgenic plants (bottom left and right) carrying sense construct of calmodulin. The potatoes from the transgenic plants are from the plants shown in FIG. 3A (also see FIG. 4, lanes 4–6).

Figure 6:
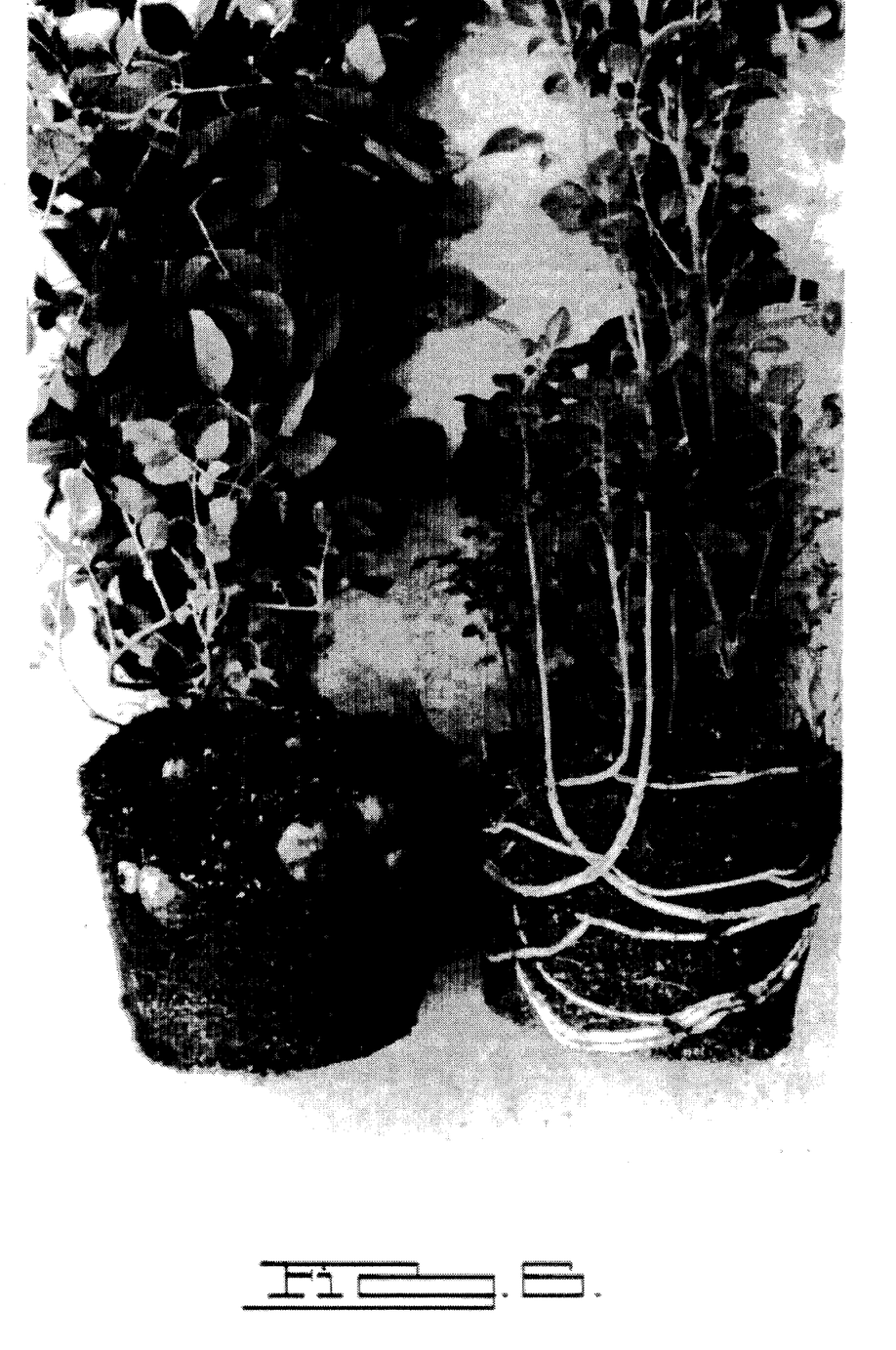
FIG. 6 is a photograph of a control plant and a transgenic plant carrying calmodulin sense strand constructs, expressing the highest amount of calmodulin mRNA.

FIG. 6 shows a control plant on the left with normal development of potatoes and a transgenic plant on the right carrying sense construct expressing the highest amount of calmodulin mRNA, as shown in FIG. 4, lanes 7 and 8. As shown in FIG. 6, there is significant alterations in growth and development, in particular, there is a lack of normal potatoes.

Figure 7:
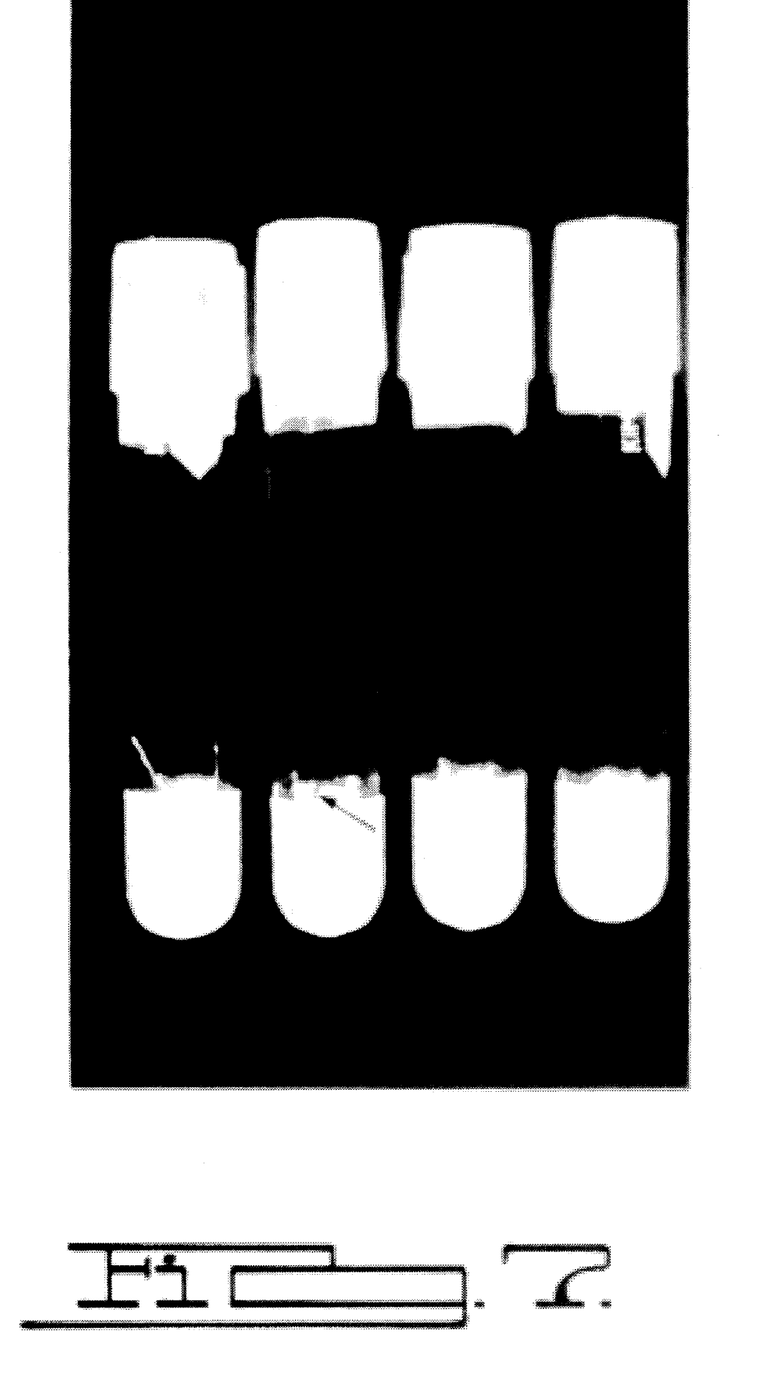
FIG. 7 is a photograph showing stem cuttings from a control and plants carrying calmodulin antisense construct fused to inducible promoter, patatin.

FIG. 7 is a photograph showing stem cuttings from plants carrying calmodulin antisense construct fused to inducible promoter, patatin. The control cutting is shown on the left and three independent transgenic cuttings are on the right. As shown in FIG. 7, there is rapid tuber formation (arrow) without stem elongation in transgenic cuttings.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

We claim:

1. A method for increasing stem and tuber elongation in a potato plant relative to a control plant, comprising the steps of introducing a nucleic acid construct into a potato plant cell and growing the cell into a plant, wherein the nucleic acid construct comprises a nucleotide sequence that encodes the protein of Sequence Listing ID No. 2.

2. The method of claim 1, wherein the nucleotide sequence is isolated from nature.

3. The method of claim 1, wherein the nucleic acid construct is synthetic.

4. A transgenic potato plant produced by the method of claim 2.

5. A transgenic potato plant comprising a nucleic acid construct, wherein the nucleic acid construct comprises a nucleotide sequence that encodes the protein of Sequence Listing ID No. 2, and wherein the nucleotide sequence is isolated from nature or is synthetic.

6. The method of claim 1, wherein the nucleotide sequence is Sequence Listing ID No. 1.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 906 base pairs
        ( B ) TYPE: nucleic acid
        ( C ) STRANDEDNESS: both
        ( D ) TOPOLOGY: linear     ( i i ) MOLECULE TYPE: cDNA     ( i i i ) HYPOTHETICAL: NO     ( v i ) ORIGINAL SOURCE:
        ( A ) ORGANISM: Solanum tuberosum
        ( C ) INDIVIDUAL ISOLATE: p-PCM- 1

( i x ) FEATURE:
        ( A ) NAME/KEY: CDS
        ( B ) LOCATION: 81..530

( x i ) SEQUENCE DESCRIPTION: SEQ ID NO:1:

```
TTTTGAGGAG AGAGATAAAA CTCAAATCAC ATACATATTA GTACTTAACT GTACAGCTGT          60

TTCTAGGAGT ACGAAAAAAA ATG GCA GAG CAG CTG ACG GAG GAG CAG ATC            110
                      Met Ala Glu Gln Leu Thr Glu Glu Gln Ile
                       1               5                  10

GCC GAG TTC AAG GAA GCT TTT AGC CTT TTC GAC AAG GAT GGC GAT GGC          158
Ala Glu Phe Lys Glu Ala Phe Ser Leu Phe Asp Lys Asp Gly Asp Gly
                15                  20                  25

TGT ATT ACT ACC AAG GAG TTG GGA ACA GTG ATG AGA TCA CTT GGT CAG          206
Cys Ile Thr Thr Lys Glu Leu Gly Thr Val Met Arg Ser Leu Gly Gln
            30                  35                  40

AAT CCC ACT GAA GCT GAA CTA CAG GAT ATG ATC AGT GAA GCT GAT GCT          254
Asn Pro Thr Glu Ala Glu Leu Gln Asp Met Ile Ser Glu Ala Asp Ala
        45                  50                  55

GAT CAG AAT GGA ACC ATT GAT TTT CCA GAG TTC TTG AAT CTG ATG GCA          302
Asp Gln Asn Gly Thr Ile Asp Phe Pro Glu Phe Leu Asn Leu Met Ala
    60                  65                  70

CGT AAG ATG AAG GAC ACT GAT TCT GAG GAG GAA CTC AAA GAG GCT TTC          350
Arg Lys Met Lys Asp Thr Asp Ser Glu Glu Glu Leu Lys Glu Ala Phe
75                  80                  85                  90

AAG GTT TTC GAT AAA GAT CAG AAT GGC TTT ATT TCT GCA GCT GAG CTT          398
Lys Val Phe Asp Lys Asp Gln Asn Gly Phe Ile Ser Ala Ala Glu Leu
                95                 100                 105

CGT CAT GTA ATG ACA AAC CTT GGA GAG AAG CTG ACT GAT GAA GAG GTG          446
Arg His Val Met Thr Asn Leu Gly Glu Lys Leu Thr Asp Glu Glu Val
            110                 115                 120

GAT GAG ATG ATC CGA GAG GCA GAT ATT GAT GGT GAT GGG CAA GTT AAT          494
Asp Glu Met Ile Arg Glu Ala Asp Ile Asp Gly Asp Gly Gln Val Asn
        125                 130                 135

TAT GAG GAG TTT GTC CGT ATG ATG CTT GCC AAG TGATGGCTTA AGATTCTCTT        547
Tyr Glu Glu Phe Val Arg Met Met Leu Ala Lys
    140                 145                 150

AGCTACTGTC TAATTTATGA TGGCCGCTTA GTTACTACAA CTTCTAGCTG GCAGTTATAT        607

TCTGTTCTGT TAAGACAAAC AAATGTGTCG TATGGTTTTA CTAGCATCTA GACTCCTTTC        667

AGTTTTATGT TAACTTATGG ACTACAGGTG TATGCTGCTT TAGTCCCTTG CCCATCCAGA        727

GGGGAAAAGA AAAGGAGAAA TTAGATAGTT CATTCGTAAT ATCTTGTTAG TTGCCTTGGT        787

TTCTTTCCAG GCTACAGTCT GTATGTGTTT CACTGTCTCT AACTGTTATA TTTCCCGTTT        847

CTGGTTTTCG CTTTTATCAC TGATTAATGG GAAGGTCAAA TGCAAGGTGA TTATTTCCT        906
```

( 2 ) INFORMATION FOR SEQ ID NO:2:

( i ) SEQUENCE CHARACTERISTICS:
        ( A ) LENGTH: 149 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:2:

```
Met Ala Glu Gln Leu Thr Glu Glu Gln Ile Ala Glu Phe Lys Glu Ala
 1               5                  10                  15
Phe Ser Leu Phe Asp Lys Asp Gly Asp Gly Cys Ile Thr Thr Lys Glu
                20                  25                  30
Leu Gly Thr Val Met Arg Ser Leu Gly Gln Asn Pro Thr Glu Ala Glu
            35                  40                  45
Leu Gln Asp Met Ile Ser Glu Ala Asp Ala Asp Gln Asn Gly Thr Ile
        50                  55                  60
Asp Phe Pro Glu Phe Leu Asn Leu Met Ala Arg Lys Met Lys Asp Thr
 65                  70                  75                  80
Asp Ser Glu Glu Glu Leu Lys Glu Ala Phe Lys Val Phe Asp Lys Asp
                85                  90                  95
Gln Asn Gly Phe Ile Ser Ala Ala Glu Leu Arg His Val Met Thr Asn
               100                 105                 110
Leu Gly Glu Lys Leu Thr Asp Glu Glu Val Asp Glu Met Ile Arg Glu
           115                 120                 125
Ala Asp Ile Asp Gly Asp Gly Gln Val Asn Tyr Glu Glu Phe Val Arg
       130                 135                 140
Met Met Leu Ala Lys
145
```